United States Patent [19]

Marcoux

[11] Patent Number: 5,232,950

[45] Date of Patent: Aug. 3, 1993

[54] METHOD FOR USING KETAMINE FOR PREVENTION OR REDUCTION OF THE EFFECTS OF STROKE IN A SUBJECT HAVING INCREASED RISK FOR STROKE

[75] Inventor: Frank W. Marcoux, Ann Arbor, Mich.

[73] Assignee: Warner-Lambert Company, Morris Plains, N.J.

[21] Appl. No.: 463,865

[22] Filed: Jan. 5, 1990

Related U.S. Application Data

[63] Continuation of Ser. No. 175,645, Mar. 21, 1988, abandoned, which is a continuation of Ser. No. 57,613, Jun. 15, 1987, abandoned, which is a continuation-in-part of Ser. No. 890,246, Jul. 24, 1986, abandoned.

[51] Int. Cl.$^5$ .................. A61K 31/55; A61K 31/135
[52] U.S. Cl. ..................................... 514/646; 514/221
[58] Field of Search ................................ 514/646, 221

[56] References Cited

PUBLICATIONS

Physicians' Desk Reference; 38th Ed. (1984) pp. 745–746.

Primary Examiner—Allen J. Robinson
Attorney, Agent, or Firm—Ronald A. Daignault

[57] ABSTRACT

The present invention is a method of use for the prevention or reduction of the effects of stroke in a subject susceptible to or at risk of stroke with ketamine. The method also includes combination of ketamine and a benzodiazepine in the use.

10 Claims, No Drawings

METHOD FOR USING KETAMINE FOR PREVENTION OR REDUCTION OF THE EFFECTS OF STROKE IN A SUBJECT HAVING INCREASED RISK FOR STROKE

This is a continuation of U.S. Ser. No. 07/175,645 filed Mar. 21, 1988, now abandoned, which is a continuation of U.S. Ser. No. 07/057,613 filed Jun. 15, 1987, now abandoned, which is a continuation of U.S. application Ser. No. 07/175,645 filed Mar. 21, 1988 which is a continuation of U.S. Ser. No. 07/057,613 filed Jun. 15, 1987 which is a continuation-in-part of U.S. Ser. No. 06/890,246 filed Jul. 24, 1986, now abandoned.

BACKGROUND OF THE INVENTION

The present invention relates to a method of use in the prevention of or limiting of brain injury due to stroke, preferably as an anesthetic in a subject having an increased risk for stroke, comprising administering to said subject a compound, ketamine, in an effective amount for preventing or reducing the effect of stroke. The compound may be administered in admixture with a pharmaceutically acceptable carrier in a unit dosage form.

Ketamine is well known as a general anesthetic. See, for example, paragraph "5133.Ketamine," *The Merck Index*, 10th edition, published by Merck and Company, Inc., Rahway, N.J., (1983) page 5138.

This invention is not suggested by the disclosure in, thus is not obvious over the following publications: D. Lodge, et al, "Reduction of Ischemia Induced Brain Damage and of Glutamate Induced Calcium Uptake by Subanesthetic Concentrations of Ketamine," *Neuro-Science Letters*, Abstracts of the Fourth National Meeting of the Brain Research Association, Birmingham, UK, Apr. 14-16, 1986, supplement 24 (1986), page S35. S. M. Rothman, et al, "Ketamine Blocks Anoxic Neuronal Death in vitro," *Stroke, A Journal of Cerebral Circulation*, Volumes 17, number 1, January-February (1986), 11th International Joint Conference on Stroke and Cerebral Circulation, p. 124. Particularly, the publications do not disclose or make obvious protective benefits of ketamine as regards stroke because the references do not teach that critical administration of the present invention is before in time the incidence of the stroke and in an amount that is at least sufficient to be said to be behaviorally active in the subject of the stroke.

Thus, the present invention relates to the now discovered novel method of use for the prophylactic treatment of stroke with a compound known as ketamine in an effective amount for preventing or reducing the effect of stroke in unit dosage form.

Additional references regarding related subject matter teach that ketamine acts as a noncompetitive N-methyl-D-aspartate antagonist (NMDA), Martin, D., et al, *Neuropharmacology*, Vol. 24, No. 10, pp 999-1003 (1985); Thomson, A. M., et al, Nature, *Vol.* 313, pp 479-481 (7 February 1985); and teach that 2-amino-7-phosphoheptanoic acid (2-APH), also an N-methyl-D-aspartate antagonist, shows prevention of brain damage associated with stroke, SCRIP, number 1067, p 22 (Jan. 13, 1986). However, although a rationale for testing 2-APH in stroke is presented in SCRIP the reference does not suggest the use of ketamine as such for treatment of stroke, and particularly, there is no disclosure to make obvious the critical administration of the present invention.

Further, the present invention is the use of ketamine for treating a subject at risk of stroke as disclosed herein wherein the treatment is administration of ketamine in combination with a benzodiazepine, such as diazepam. Again, although references show the combined use of ketamine and benzodiazepines, Langrehr, D., et al, *Acta Anaesthesiologica Belgica*, number 2, pp 165-187 (June 1984), the combination is not obvious for use in the present invention administration of ketamine.

SUMMARY OF THE INVENTION

Accordingly, the present invention relates to a method of use for the prophylactic treatment of stroke in a subject susceptible thereto, comprising administering to said subject an antistroke effective amount of ketamine. The ketamine may be administered in admixture with a pharmaceutically acceptable carrier in a unit dosage form.

Ketamine is also known as dl 2-(o-chlorophenyl)-2-(methylamino)cyclohexanone or 2-(2-chlorophenyl)-2-(methylamino)cyclohexanone or 2-(methylamino)-2-(2-chlorophenyl)cyclohexanone. This invention is also understood to include the hydrochloride salt therefor.

Ketamine may be prepared by a method disclosed in U.S. Pat. No. 3,254,124 which is incorporated herein by reference.

Ketamine is also available commercially.

DETAILED DESCRIPTION

Ketamine; having use for the method of treating stroke of the present invention, is known for use as a general anesthetic, more particularly, ketamine is a nonbarbiturate anesthetic having a rapid acting general anesthetic action producing an anesthetic state characterized by profound analgesia, normal pharngeallaryngeal reflexes, normally or slightly enhanced skeletal muscle tone, cardiovascular and respiratory stimulation, and occasionally a transient and minimal respiratory depression. The previously known effects do not suggest the present use of prophylactic treatment for stroke. The other words ketamine for use in the present invention has heretofore not been recognized or been made obvious.

The present invention, however, relates to the discovery that ketamine as defined above, has activity for a novel method of use specifically for treating subjects susceptible to strokes. The stroke as referred to in the present invention is a cerebral vascular disease and may also be referred to as a cerebral vascular accident (CVA) and specifically includes acute thromboembolic stroke. Also included in cerebral vascular disease are transient cerebral ischemic attacks and other cerebral vascular problems accompanied by cerebral ischemia. Particularly, a subject susceptible to such strokes for the practice of the present invention may be the subject undergoing carotid endarterectomy, specifically, or other cerebrovascula or vascular surgical procedures, in general, or diagnostic vascular procedures including cerebral angiography in some cases, and the like. Specifically, ketamine may be used as an anesthetic or adjunct to anesthesia in such procedures. An ordinary skilled physician would be able to determine the appropriate situation in which subjects susceptible to or at risk of stroke for administration of ketamine by the methods of the present invention.

Subjects as used herein are mammals, including humans.

According to this invention, ketamine, which is an agent for treating a subject susceptible to stroke as defined herein, is administered in an effective amount which comprises a total intravenous or intramuscular injection of ketamine. Such amount ranges from an amount which can be said to be behaviorally active in the subject to an amount providing complete anesthetic effect.

Generally, administration of ketamine in anesthetic amounts according to the present invention is within those known and described for known uses. That is, because of rapid induction following the initial intravenous injection, the subject should be in a supported position during administration.

The onset of action of ketamine is rapid; an intravenous dose of 2 mg/kg (1 mg/lb) of body weight usually produces surgical anesthesia within 30 seconds after injection, with the anesthetic effect usually lasting five to ten minutes. If a longer effect is desired, additional increments can be administered intravenously or intramuscularly to maintain anesthesia without significant cumulative effects.

Intramuscular doses, from experience primarily in children, in a range of 9 to 13 mg/kg (4 to 6 mg/lb) usually produce surgical anesthesia within three to four minutes following injection, with the anesthetic effect usually lasting 12 to 25 minutes.

As with other general anesthetic agents, the individual response to ketamine is somewhat varied depending on the dose, route of administration, and age of subject, so that dosage recommendation cannot be absolutely fixed. The drug should be titrated against the patient's requirements.

Induction

Intravenous Route: The initial dose of ketamine administered intravenously may range from 1 mg/kg to 4.5 mg/kg (0.5 to 2 mg/lb). The average amount required to produce five to ten minutes of surgical anesthesia has been 2 mg/kg (1 mg/lb).

Alternatively, in adult patients an induction dose of 1.0 mg to 2.0 mg/kg intravenous ketamine at a rate of 0.5 mg/kg/min may be used for induction of anesthesia. In addition, diazepam in 2 mg to 5 mg doses, administered in a separate syringe over 60 seconds, may be used. In most cases, 15.0 mg of intravenous diazepam or less will suffice. The incidence of psychological manifestations during emergence, particularly dream-like observations and emergence delirium, may be reduced by this induction dosage program.

The 100 mg/ml concentration of ketamine should not be injected intravenously without proper dilution. It is recommended the drug be diluted with an equal volume of either sterile water for injection, USP, normal saline, or 5% dextrose in water.

Rate of Administration: It is recommended that ketamine be administered slowly (over a period of 60 seconds). More rapid administration may result in respiratory depression and enhanced pressor response.

Intramuscular Route: The initial dose of Ketalar administered intramuscularly may range from 6.5 to 13 mg/kg (3 to 6 mg/lb) A dose of 10 mg/kg (5 mg/lb) will usually produce 12 to 25 minutes of surgical anesthesia.

Maintenance of Anesthesia

The maintenance dose should be adjusted according to the patient's anesthetic needs and whether an additional anesthetic agent is employed.

Increments of one-half to the full induction dose may be repeated as needed for maintenance of anesthesia. However, it should be noted that purposeless and tonic-clonic movements of extremities may occur during the course of anesthesia. These movements do not imply a light plane and are not indicative of the need for additional doses of the anesthetic. It should be recognized that the larger the total dose of Ketalar administered, the longer will be the time to complete recovery.

Adult patients induced with ketamine augmented with intravenous diazepam may be maintained on Ketalar given by slow microdrip infusion technique at a dose of 0.1 to 0.5 mg/minute, augmented with diazepam 2 to 5 mg administered intravenously as needed. In many cases 20 mg or less of intravenous diazepam total for combined induction and maintenance will suffice. However, slightly more diazepam may be required depending on the nature and duration of the operation, physical status of the patient, and other factors. The incidence of psychological manifestations during emergence, particularly dream-like observations and emergence delirium, may be reduced by this maintenance dosage program.

Dilution: To prepare a dilute solution containing 1 mg of ketamine per ml, aseptically transfer 10 ml (50 mg per ml Steri-Vial) or 5 ml (100 mg per ml Steri-Vial) to 500 ml of 5% dextrose injection, USP, or sodium chloride (0.9%) injection, USP (normal saline), and mix well. The resultant solution will contain 1 mg of ketamine per ml.

The fluid requirements of the patient and duration of anesthesia must be considered when selecting the appropriate dilution of ketamine. If fluid restriction is required, ketamine can be added to a 250 ml infusion as described above to provide a ketamine concentration of 2 mg/ml.

Ketamine Steri-Vials, 1% mg/ml are not recommended for dilution.

Additionally, administration of ketamine according to the present invention may be in behaviorally active amounts. That is, the present invention may be a method to administer ketamine in amounts less than that sufficient to anesthetize the subject of the present invention. Such amount however, must be at least the amount necessary to initiate behavioral changes, such as, for example impairment of response, in the subjects selected for the practice of the invention as described above.

Thus, the range of dosages for the methods of using ketamine in the present invention may be such that other anesthetics are administered in combination with ketamine.

Therefore, the present invention is also a method of using ketamine for prevention or reduction of the effects of a stroke in combination with supplemental anesthetics.

Supplementary Anesthetics

It is known that ketamine is clinically compatible with the commonly used general and local anesthetic agents when an adequate respiratory exchange is maintained.

The regimen of a reduced dose of ketamine, i.e., in an amount that is behaviorally active in the subject of the present invention, supplemented with diazepam can be used to produce anesthesia by combination with other agents such as nitrous oxide and oxygen.

Such dosages specifically for an adult human can be used in a single administration of the total amount or in divided doses. Generally, a large initial dose is followed by a series of lesser doses to maintain plasma blood levels.

The preferred dosage for the present invention is an anesthetic amount of ketamine.

The preferred route of administration is that deemed preferred as judged by the physician. For example, subjects in surgery which are susceptible to stroke, intravenous administration may be preferred. Additionally, in high risk stroke patients, such as, for example, patients entering surgery, intravenous administration may also be preferred.

On the other hand, during maintenance doses, intramuscular administration may be preferred. Variations within these dosages may depend on the age, size, or individual characteristics of the subject being treated. In particular subjects it may be preferable to begin dosages at the lower level critically acceptable from the presently known anesthetic utility and to monitor side effects using amounts to the desired dosage critical for the at risk patient receiving treatment for stroke.

The pharmaceutical compositions for the method of use can take any number of a wide variety of parenteral dosage forms. The dosage forms comprise as the active component, ketamine as defined above. Such pharmaceutical compositions are from among those of the ordinary skill in the art. Particularly the compositions of ketamine which are commercially available are compositions for use in the method of use in the present invention.

For preparing pharmaceutical compositions, one uses inert, pharmaceutically acceptable carriers that are liquid. Such liquid form preparations include, solutions, suspensions, and emulsions. As an example, may be mentioned, water or water propylene glycol solutions for parenteral injection. Liquid preparations can also be formulated in solution in aqueous polyethylene glycol solution.

Preferably, the pharmaceutical preparation is in unit dosage form. In such form the preparation is subdivided into unit doses containing appropriate quantities of active components. Unit dosage form can be a packaged preparation, for example, powders in vials or ampoules. The unit dosage form can also be a syringe in packaged form.

Generally, the pharmaceutical compositions preferably are constituted so they can be administered parenterally. Solutions of the active compounds as free bases or pharmaceutically acceptable salts preferably hydrogen chloride, can be prepared in water suitably mixed with the surfacant such as hydroxypropylcellulose. Dispersions can also be prepared in glycerol liquid polyethyleneglycols and mixtures thereof and in oils. Under ordinary conditions of storage and use these preparations contain a preservative to prevent the growth of microorganisms.

The pharmaceutical form suitable for injectable use include sterile aqueous solutions or dispersions and sterile powders for the extemporaneous preparation of sterile injectable solutions or dispersions. In all cases the form must be sterile and must be fluid to the extent that easy syringability exists, it must be stable under the conditions of manufacture and storage, and must be preserved against the contaminating action of microorganisms such as bacteria and fungi. The carrier can be a solvent or dispersion medium containing, for example, water, ethynol, polyl (for example glycerol, propyleneglycol, and liquid polyethyleneglycol, and the like), suitable mixtures thereof, and vegetable oils. The proper fluidity can be maintained for example by the use of a coating, such a lithicin? by the maintenance of the required particle size in the case of dispersion and by the use of surfacants. The prevention of the action of microorganisms can be brought about by various antibacterial and antifungal agents, for example, paragens, chlorobutanol, phenyl, sorbic acid, thirmerosal, and the like. In many cases it will be preferable to include tonic agents, for example, sugars or sodium chloride. Prolonged absorption of the injectable compositions of agents delaying absorption, may be accomplished with for example, aluminum monostearate and gelatin.

Sterile injectable solutions are prepared by incorporating ketamine in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of the sterile powders for the preparation of sterile injectable solutions, the preferred methods of preparation and the freeze-drying techniques which yield a powder of active ingredients plus any additional desired ingredient from a previously sterile-filtered solution thereof.

As used herein "pharmaceutically acceptable carrier" includes any and all solvents dispersion medium, coatings, antibacterial and antifungal agents, isotonic and absorption delaying agents and the like. The use of such media and agents for pharmaceutically active substances is well known in th=art. Except, in so for as any conventional media is incompatible with the active ingredient, its use in the therapeutic compositions is contemplated. Supplementary active ingredients can also be incorporated into the compositions.

It is especially advantageous to formulate parenteral or intravenous compositions in dosage unit form for ease of administration and uniformity of dosage. Dosage unit form as used herein refers to physically discrete units suitable as unitary dosages for the mammalian subjects to be treated; each unit containing a predetermined quantity of active materials calculated to produce the desired therapeutic effect as described above in association with the required pharmaceutical carrier. The specification for the novel dosage unit forms of the invention are dedicated by and directly dependent on a) the unique characteristics of the active materials and the particular therapeutic effect to be achieved and b) the limitation inherent in the art of compounding such active materials for the treatment of stroke in living subjects having a stroke condition in which bodily health is impaired or is anticipated as herein disclosed in detail.

The principle active ingredients are compounded for convenient and effective administration in effective amounts with a suitable pharmaceutically acceptable carrier in unit dosage form as herein before disclosed. A unit parenteral dosage form can, for example contain the principle active compound, ketamine, ranging from 10, 50, or 100 mg with from 10 mg being preferred. Expressed in proportions the ketamine is generally present in from 10, 50, or 100 mg/ml of carrier. The parenteral doses for humans to be treated with ketamine ranges from 10 to 100 mg/kg.

Thus, the preferred dosage range in the unit dosage form is that which results in stable anesthesia. On the other hand, if ketamine is used with one or more additional anesthetics the dosage range in the unit dosage form may be that determined to cause a behavioral change in the subject of the invention.

The usefulness of the active compound ketamine in the method of use for treating subjects susceptible or at risk of stroke of the present invention is demonstrated by administration of the active compound ketamine in an essentially pharmacological test procedure as described and illustrated in the following assay.

ASSAYS

Temporary Bilateral Carotid Occlusion (BCO) in Gerbils and Subsequent Behavioral Testing as a Screen for Drugs Active in the Prevention or Reducing the Effects of Stroke The gerbil is well established as a convenient model for the induction of cerebral ischemia as well as abrupt occlusive stroke (Molinari, G. F. and Laurent, J. P.: A classification of experimental models of brain ischemia. Stroke 7(1): 14–17, 1976). The gerbil, unlike most other mammals, has an incomplete circle of Willis, often lacking adequately patent posterior communicating arteries. Thus, one can easily produce brain ischemia by occluding the common carotid arteries.

Chandler and Carney (Chandler, M. J. and Carney, J. M.: Alterations in spontaneous locomotor activity following transient cerebral ischemia in the unanesthetized gerbil. American Society for Pharmacology and Experimental Therapeutics, The Pharmacologist Vol. 26, No. 3, Abst. No. 494, 1984) and Tang, et al, (Tang, A. H., Hudson, L., and Salvatierra, A.: Behavioral sequelae from 5-minute bilateral carotid occlusion in the mongolian gerbil. Society for Neuroscience Abstracts, Vol. 10, Part 1, 1984) show that a temporary bilateral carotid artery occlusion in the gerbil results in animals that appear grossly normal but exhibit greatly increased locomotor activity.

Therefore, adult male gerbils (Meriones unguiculatus) weighing 45–65 g (8–12 weeks old) are housed ten per cage in a constant temperature environment with a 12 hour light-dark cycle. Food and water are provided ad libitum. The gerbils are allowed to acclimate to the animal housing facility for a minimum of five days before being used in any experimental procedures.

Experimental gerbils are anesthetized by inhalation of ether. A ventral, cervical midline incision is made. Both the right and left common carotid arteries are exposed and isolated from surrounding nerves, vessels, and tissue. One aneurysm clip (7.5 mm × 1.0 mm) is placed on each carotid artery, effectively shutting off blood flow to both cerebral hemispheres. The incision is closed with 9 mm stainless steel wound clips, allowing the aneurysm clips to protrude from the incision for later removal. The entire procedure lasts approximately four minutes. The clips are left in place for ten minutes and then removed, restoring cerebral blood flow. Published studies show that blood blow can be restored completely after bilateral carotid occlusion of one hour or more.

Gerbils surviving the ten minute bilateral carotid occlusion procedure (BCO) are placed in darkened activity chambers, one animal per chamber. The chambers are lined by six evenly spaced photo cells. Activity is monitored for thirty minutes and recorded by microcomputer. One activity count is equivalent to braking any six photobeams.

In a preliminary time course study the activity of a group of fourteen gerbils is monitored on Days 1, 2, 3, 4, 7, 10, and 14 after they had undergone the BCO procedure. Exploratory locomotor activity as measured in the above described chambers is increased at each time point after BCO relative to sham operated or control unoperated gerbils. The sham operation consists of the ventral, cervical midline incision, carotid exposure, and separation from surrounding tissue.

The protocol for screening compounds in this model is to dose the animals with the test compound or vehicle 30 minutes prior to the BCO procedure. As controls, one group of gerbils receive vehicle and a second group get the test compound. These controls do not undergo the BCO procedure nor are they given a sham operation. The sham operation is determined to have no effect on locomotor activity when compared to nonsurgically manipulated animals.

The gerbils are given a drug washout period (typically 48 hours) before their activity is monitored. This washout period is intended to prevent any activity changes which might be the result of a nonspecific drug effect such as sedation, ataxia, or stimulation. Following the washout period, activity is monitored for 30 minutes.

Ten minutes of BCO performed under ether anesthesia results in 20–40% mortality. The surviving gerbils are grossly indistinguishable from sham operated controls or from nonsurgically manipulated animals. However, the surviving gerbils when tested in the locomotor activity assay are found to show significant increases in locomotor activity relative to sham operated controls. Both the sham operated animals and the nonsurgically manipulated gerbils exhibit equivalent activity counts indicating that the surgical procedure itself had no effect on activity.

The preliminary time course study reveals that on Days 1–4 the gerbils that undergo BCO show 100–150% increases in locomotor activity relative to controls.

The BCO procedure as reported here produces a significant, reproducible increase in locomotor activity which is objectively measurable. The fact that the increased activity is measurable for at least four days after the occlusion allows some flexibility with regard to dosing schedule and length of drug washout. Activity is monitored 24 or 48 hours after the BCO.

The literature indicates that the altered locomotor activity pattern after BCO is the result of bilateral damage to the CA 1 region of the hippocampus.

The protection from ischemia presumed to occur with pentobarbital anesthesia during the BCO procedure is consistent with reports in the literature (Hoff, Julian T.: Resuscitation in focal brain ischemia. Critical Care Medicine, Vol. 6, No. 4, 1978). These suggest cerebral protection during ischemia by barbiturate induced metabolic suppression.

The 20–40% mortality among gerbils having undergone the ten minute BCO likely corresponds to a subpopulation of gerbils known to be more sensitive to cerebral ischemia produced by carotid occlusion.

The measurement of postischemia functional performance of the BCO assay is thus an indicator of drug treatment efficacy for ketamine as follows:

Ketamine hydrochloride is administered in a first study in the BCO assay as a pretreatment (30 minutes before) to BCO at 100, 200, and 300 mg/kg, IP. The results of the first study is shown in Table 1.

TABLE 1

Effects of Ketamine[1] Hydrochloride
on Abnormal Increases in Exploratory
Locomotor Activity in Gerbils After
Temporary Global Cerebral Ischemia

| Treatment | Locomotor[2] Activity Expressed as Percent Increase Over that Observed in Vehicle Control Gerbils |
|---|---|
| Vehicle Treated Controls (n = 9) | 0.0 |
| BCO[3] Controls (n = 8) | 114.0% |
| KET 100 mg/kg (n = 7) | 59.0% |
| KET 200 mg/kg (n = 9) | −10.0%* |
| KET 300 mg/kg (n = 8) | 11.0%* |

[1]Ketamine hydrochloride (KET) was administered 30 minutes prior to BCO at 100, 200, or 300 mg/kg, IP.
[2]Locomotor activity was measured 48 hours after BCO according to the protocol which describes this assay.
[3]BCO controls were vehicle treated gerbils subjected to ten minutes of bilateral carotid occlusion (BCO) under brief ether anesthesia.
*Actual activity values were reduced relative to BCO controls (p < 0.05) and not different from vehicle treated controls.
Conclusion: The 200 and 300 mg/kg doses of ketamine prevented the global cerebral ischemia-induced increase (114%) in exploratory locomotor activity 48 hours after BCO.

One-hundred mg/kg ketamine inhibited the ischemia-induced locomotor increase by 50% (marginal activity) and both 200 and 300 mg/kg ketamine pretreatments abolished the abnormal locomotor activity increase (statistically significant activity). Thus, the 200 and 300 mg/kg pretreatments with ketamine totally protected the brain from ischemic injury according to this protocol.

In the repeat study the same protective effects are noted for 150 and 200 mg/kg pretreatments with ketamine. The results of the repeat study are shown in Table 2.

TABLE 2

Effects of Ketamine[1] Hydrochloride
on Abnormal Increases in Exploratory
Locomotor Activity in Gerbils After
Temporary Global Cerebral Ischemia

| Treatment | Locomotor[2] Activity Expressed as Percent Increase Over that Observed in Vehicle Control Gerbils |
|---|---|
| Vehicle Treated Controls (n = 9) | 0.0% |
| BCO[3] Controls (n = 9) | 148.2% |
| KET 100 mg/kg | 52.0% |
| KET 150 mg/kg | 41.0%* |
| KET 200 mg/kg | 4.0%* |

[1]Ketamine hydrochloride (KET) was administered as the 30 minutes prior to BCO at 100, 150, or 200 mg/kg, IP.
[2]Locomotor activity was measured 14 days after BCO according to the protocol which describes this assay.
[3]BCO controls were vehicle treated gerbils subjected to ten minutes of bilateral carotid occlusion (BCO) under brief ether anesthesia.
*Actual activity values were reduced relative to BCO controls (p < 0.05) and not different from vehicle treated controls.
Conclusion: The 150 and 200 mg/kg doses of ketamine prevented the global cerebral ischemia-induced increase (148%) in exploratory locomotor activity 14 days hours after BCO.

In addition, in this study the protective effects were observed to persist at 7 and 14 days after temporary BCO. However, as in the previous study ketamine is given only once, 30 minutes prior to BCO.

Finally, a third study shows by comparison that protective effects are not found in the same assay but having administration of the ketamine 30 minutes after temporary global cerebral ischemia. The results of the third study are shown in Table 3.

TABLE 3

Effects of Ketamine[1] Hydrochloride
on Abnormal Increases in Exploratory
Locomotor Activity in Gerbils After
Temporary Global Cerebral Ischemia

| Treatment | Locomotor[2] Activity Expressed as Percent Increase Over that Observed in Vehicle Control Gerbils |
|---|---|
| Vehicle Treated Controls (n = 7) | 0.0% |
| BCO[3] Controls (n = 8) | 107.0% |
| KET 100 mg/kg | 76.0% |
| KET 200 mg/kg | 55.0% |

[1]Ketamine hydrochloride (KET) was administered as a treatment 30 minutes after BCO at 100, or 200 mg/kg IP.
[2]Locomotor activity was measured 48 hours after BCO according to the protocol which describes this assay.
[3]BCO controls were vehicle treated gerbils subjected to ten minutes of bilateral carotid occlusion (BCO) under brief ether anesthesia.
Conclusion: Ketamine administered after BCO as a treatment does not significantly prevent the abnormal increase, in exploratory locomotor activity; however, there was an attenuation of this increase at 200 mg/kg.

Combined Middle Cerebral and Ipsilateral Common
Carotid Occlusion in the Rat as a Screen for
Compounds Active in the Treatment of Stroke
(MCAO)

Occlusion of the proximal part of the middle cerebral artery (MCA) is a common cause of stroke in man and can be accomplished surgically in experimental animals. This technique, though technically feasible in the rat (A. Tamura, et al, Focal Cerebral Ischemia in the Rat: 1. Description of Technique and Early Neuropathological Consequences Following Middle Cerebral Artery Occlusion. *J. Cereb. Blood Flow Metab.* 1:53-60, 1981), is very difficult and time-consuming. It has been reported that a distal occlusion of the MCA 5 mm from its origin at the circle of Willis does not consistently result in infarction (P. Coyle, Middle Cerebral Artery Occlusion in the Young Rat. *Stroke* 13:6 1982). In the present assay distal MCA occlusion is combined with ipsilateral common carotid ligation in an attempt to produce reproducible, focal cerebral ischemic infarcts.

Adult male Fisher (F-344) rats (250–300 g) are anesthetized in a box containing halothane and then moved to a small animal anesthetic mask (D. E. Levy, et al, A Mask for Delivery of Inhalation Gases to Small Laboratory Animals. *Laboratory Animal Science*, Volume 30, 5:868–870, 1980) to which 1.5% halothane in room air is provided for spontaneous inspiration. The skin on the ventral side of the neck and the left temporal-parietal region is shaved. An incision is made in the neck and the left common carotid artery is doubly ligated and cut between the sutures. The incision is infiltrated with local anesthetic and closed with 4-0 silk. Another incision is then made behind the left eye and the skin is held back with retracters. The exposed temporalis muscle is electrocauterized (Jarit Bipolar Coagulator) and partially removed. Deep surgery is performed with the air of a Zeiss OPMI 99 surgical microscope. A 1 to 2-mm diameter craniotomy is made about 1 mm anterior to where the rostral end of the zygoma fuses to the squamosal bone. The prevent the drill from going through the dura, the burr hole is not drilled completely through the skull. Bone remaining after drilling is removed with forceps. The dura is pierced and reflected with a fine probe.

At this point the rat is injected with 0.3 ml of 2% Evans blue dye in saline via the tail vein. Evans blue binds to serum albumin and will not pass the blood-brain barrier unless damage has occurred, such as damage induced by ischemia. A small hook is then positioned under the MCA and the MCA is lifted away from the cortex. A jeweler-type bipolar forceps is introduced and the MCA is electrocauterized and separated Gelfoam ® is put over the craniotomy nd wound is closed with 4-0 silk. The rats are then taken off the halothane and allowed to wake up. Total anesthesia time is typically 30 minutes. Animals undergoing this procedure (MCAO rats) awake from anesthesia within ten minutes of breathing room air along again and are grossly indistinguishable from unoperated rats.

On Day 2 following MCA occlusion, the rats were anesthetized with ketamine (150 mg/kg, IP) and sacrificed. Cerebral tissue fixation is initiated by perfusion of 10% neutralized, buffered formalin for five minutes. Brains are removed and stored in the fixative until analysis.

For evaluation of the extent of cerebral ischemic injury the brains were cut coronally in three different locations. The first section is at the level where the MCA was ligated. The other two sections are 2 mm anterior and 2 mm posterior to the first. Using an aus-Jena Citoval ® microscope with a drawing tube and an Apple II plus computer with a Houston Instrument digitizing pad, we employed a software routine to measure the area of the ischemic damage as indicated by th extent of Evans blue tissue extravasation. The software package is purchased from R+M Biometrics (Nashville, Tenn.) and is titled Bioquant II. From the lesion ares ($mm^2$) obtained from the Bioquant II program, we estimate the hemispheric extent ($mm^3$) of ischemic damage between the anterior and posterior sections by computing and adding the volume of two truncated cones.

In preliminary experiments the extent of cerebral ischemic injury was compared to MCAO and sham-operated rats. Sham-operated rats underwent an identical surgical procedure except that the bipolar electrocautery forceps were activated away from the artery but within the subarachnoid space.

The effects of MCA and ipsilateral common carotid artery occlusion on the areas of ischemic damage are summarized as hemispheric volume of injury in the following Table 4. Thus, a comparison of infarct size in the sham-operated versus MCAO rats is shown.

TABLE 4

The Effects of Middle Cerebral and Ipsilateral Common Carotid Artery Ligation (MCAO) on Hemispheric Ischemic Damage in the Rat

| Rat # | Sham Operated Rats Hemispheric Ischemic Damage ($mm^3$) | MCAO Rats Hemispheric Ischemic Damage ($mm^3$)[1] |
|---|---|---|
| 1 | 5.80 | 63.67 |
| 2 | 3.32 | 37.74 |
| 3 | 4.50 | 37.07 |
| 4 | 10.20 | 24.40 |
| 5 | 5.61 | 45.57 |
| Mean ± SE | 5.80 ± 1.17 | *41.69 ± 6.46 |

[1]Hemispheric ischemic damage was estimated by computing a volume from the three coronal areas. Hemispheric Ischemic Damage comparisons were made using a nonpaired Students T-test.
*p < 0.01

The area of ischemic damage was significantly larger in the MCAO as compared to the sham-operated rats in the anterior and middle coronal sections, represented both as area of injury and area of injury as a percentage of the entire coronal section. The posterior coronal section showed a tendency toward a larger area of injury in MCAO animals relative to sham-operated controls. The area of the entire coronal section (infarcted and noninfarcted tissue) was 6.9% and 4.1% smaller in the anterior and posterior sections, respectively, in the MCAO versus sham operated animals. Although these decreases in coronal section area were small, they were statistically significant.

Combined middle cerebral and ipsilateral common carotid artery ligation caused ischemic cerebral tissue injury which was consistently greater in extent than that injury which occurs as a result of sham operation alone. The area of injury was greatest in the anterior and middle coronal sections, which is consistent with the area of middle cerebral arterial distribution in the rat. The biological significance of the slightly smaller anterior and posterior coronal areas (infarcted and noninfarcted tissue) in MCAO animals remains unclear.

The Bioquant II image analysis system proved useful in quantitating ischemic injury as it was identified by Evans blue extravasation (blood brain barrier disruption). The variability in extent of ischemic cerebral tissue injury in this model is small enough that it can be reasonably anticipated that successful treatment can be detected by reduction in the lesion size.

The activity of ketamine for use in the present invention is determined to be active in this screen because its administration before arterial ligations leads to a reduction in the extent of cerebral tissue injury. Such reduction is shown in the following Table 5.

TABLE 5

Effects of Ketamine[1] Hydrochloride on Infarct Size After Permanent Focal Cerebral Ischemia in Rats

| Treatment | Hemispheric[2] Infarct Volume As Percent of Historical Control Rats (n = 25) |
|---|---|
| KET 50 mg/kg (n = 5) | 105.0% |
| KET 100 mg/kg (n = 4) | 117.0% |
| KET 150 mg/kg (n = 10) | 61.0%* |

[1]Ketamine hydrochloride (KET) was administered as the 30 minutes prior to MCAO at 50, 100, or 150 mg/kg, IP. The 50 and 100 mg/kg doses did not provide adequate anesthesia and therefore, these animals received supplemental halothane anesthesia. The 150 mg/kg was an anesthetic dose.
[2]Hemispheric infarct volume was assessed quantitatively after combined middle cerebral and ipsilateral carotid artery occlusion (MCAO) according to the protocol which describes this assay.
*Actual activity values were reduced relative to historical controls (p < 0.05).
Conclusion: At 50 and 100 mg/kg there is no difference in infarct size between ketamine and halothane anesthetized rats. However, at 150 mg/kg, an anesthetic dose of ketamine, there is statistically significant (40%) reduction in hemispheric infarct volume relative to historical control halothane anesthetized animals.

However, another study here shows that protective effects are not found when administration of the ketamine is accomplished after permanent focal cerebral ischemia (MCAO). See the following Table 6.

TABLE 6

Effects of Ketamine[1] Hydrochloride Treatment on Infarct Size After Permanent Focal Cerebral Ischemia in Rats

| Treatment | Hemispheric[2] Infarct Volume As Percent of Historical Control Rats (n = 25) |
|---|---|
| KET 30 mg/kg (n = 5) | 106.0% |
| KET 67 mg/kg (n = 5) | 94.0% |
| KET 150 mg/kg (n = 10) | 108.0% |

[1]Ketamine hydrochloride (KET) was administered 30 minutes and again 24 hours after MCAO at 30, 67, or 150 mg/kg, IP.
[2]Hemispheric infarct volume was assessed quantitatively after combined middle cerebral and ipsilateral carotid artery occlusion (MCAO) according to the protocol which describes this assay.
Conclusion: Ketamine treatment after MCAO did not reduce cerebral infarct size.

Thus, in two stroke models, one which mimics cardiac arrest (near total cerebral ischemia) followed by resuscitation (BCO model in gerbils) and one which mimics thromboembolic cerebral arterial occlusion (unilateral stroke) (MCAO model in rats), pretreatment with ketamine improved clinically relevant measures of outcome.

In view of the observations that ketamine abolishes functional locomotor disturbances and decreases the area of damage when administered prior to the onset of cerebral ischemia the method of use of the present invention results in amelioration or prevention of stroke in mammals, including humans. Thus, the results of this study indicate a heretofore unknown advantage and beneficial effect for ketamine in a model of stroke as an effective agent in treating subjects susceptible to or at risk of stroke.

Combination of diazepam, a representative benzodiazepine and ketamine were studied using the methodology described above with the following variations and results.

Gerbils were administered diazepam 2 mg/kg IP. Thirty minutes later they were given Ketalar 200 mg/kg, a dose known to be active from previous studies. Additional experimental groups were given diazepam only (2 mg/kg) or Ketalar only (200 mg/kg). Control gerbils were treated with a saline vehicle and subjected to BCO (BCO Controls) or treated with vehicle but not subjected to BCO (Vehicle Controls).

TABLE 7

Effects of Diazepam/Ketamine[1]
Pretreatment on Abnormal Increases
in Exploratory Locomotor Activity
in Gerbils After Temporary
Global Cerebral Ischemia

| Treatment | Locomotor[2] Activity Expressed as Percent Increase Over that Observed in Vehicle Control Gerbils |
|---|---|
| Vehicle Treated Controls (N = 6) | 0% |
| BCO[3] Controls (N = 7) | 179% |
| KET 200 mg/kg (N = 5) | −25%* |
| DIAZ 2 mg/kg (N = 4) | 179% |
| DIAZ/KET[4] (N = 6) | −17% |

[1]Diazepam (DIAZ, 2 mg/kg) was administered IP 30 minutes before ketamine hydrochloride (KET, 200 mg/kg, IP), which was given 30 minutes before BCO.
[2]Locomotor activity was measured 24 hours after BCO according to the protocol which describes this assay.
[3]BCO controls were vehicle treated gerbils subjected to ten minutes of bilateral carotid occlusion (BCO) under brief ether anesthesia.
[4]DIAZ/KET refers to the combination treatment group.
*Actual activity values were reduced relative to BCO controls (p < 0.05) and not different from vehicle treated controls.

As shown above in Table 7, the 200 mg/kg does of ketamine prevented the global cerebral ischemia-induced increase (179%) in exploratory locomotor activity 24 hours after BCO. While diazepam treatment alone showed no activity, the combined DIAZ/KET group showed activity similar to that of the KET 200 mg/kg group.

TABLE 8

Effects of DIAZ/KET[1] on Infarct Size After
Permanent Focal Cerebral Ischemia in Rats

| Treatment | Hemispheric[2] Infarct Volume as Percent of Historical Control Rats (n = 30) |
|---|---|
| DIAZ[3] 3 mg/kg (N = 5) | 95.3% |
| DIAZ 3 mg/kg/KET 150 mg/kg | 69.2% |

[1]DIAZ/KET - Diazepam (3 mg/kg) was given IP 30 minutes before ketamine (150 mg/kg) which was given 30 minutes before MCAO. This treatment provided adequate surgical anesthesia and supplemental halothane was not required.
[2]Hemispheric infarct volume was assessed quantitatively after combined middle cerebral and ipsilateral carotid artery occlusion (MCAO) according to the protocol which describes this assay.
[3]DIAZ - diazepam alone (3 mg/kg) was given as a control group.

As shown above in Table 8, the anesthetic 150 mg/kg ketamine treatment reduced hemispheric infarct volume when diazepam was given concomitantly. Diazepam alone did not reduce hemispheric infarct volume.

I claim:

1. A method for treating a subject at risk of stroke, which subject is in need of such treatment, comprising administering to said subject ketamine in an effective amount for treating the subject at risk of stroke in a unit dosage form.

2. A method according to claim 1 wherein the effective amount is in a range from an amount effecting a behavioral change in the subject to an amount completely anesthetizing the subject.

3. A method according to claim 2 wherein the administration of ketamine is in combination with a supplemental anesthetic wherein the amount of ketamine is reduced by the amount of supplemental anesthetic used to anesthetize the subject, but no less than an amount of ketamine to provide behavioral modification in the subject.

4. A method according to claim 2 wherein the administration of ketamine is in combination with benzodiazepine having a ratio of ketamine to benzodiazepine in a range of amounts from 1 to 100 parts to 1 to 75 parts by weight.

5. A method according to claim 4 wherein the administration of ketamine is in combination with the benzodiazepine which is diazepam.

6. A method according to claim 1 wherein the amount is a behaviorally active amount.

7. A method according to claim 1 wherein the amount is 10 to 100 mg/kg administered parenterally.

8. A method according to claim 6 wherein the amount is 1 mg/kg to 4.5 mg/kg administered intravenously or 6.5 mg/kg to 13 mg/kg administered intramuscularly.

9. A method according to claim 8 wherein the amount is 2 mg/kg administered intravenously or 10 mg/kg administered intramuscularly.

10. A method according to claim 3 wherein the effective amount consists of a range from an amount effecting a behavioral change in the subject to an amount less than the amount completely anesthetizing the subject in combination with a supplemental anesthetic wherein the amount of supplemental anesthetic present is such the combination completely anesthetizes the subject.

* * * * *